United States Patent [19]
Khambay et al.

[11] Patent Number: 6,162,799
[45] Date of Patent: Dec. 19, 2000

[54] PESTICIDAL COMPOUNDS

[75] Inventors: Bhupinder P. S. Khambay, Middlesex; Duncan Batty; Stuart Cameron, both of Bedfordshire, all of United Kingdom

[73] Assignee: BTG International Limited, London, United Kingdom

[21] Appl. No.: 09/071,887

[22] Filed: May 5, 1998

Related U.S. Application Data

[60] Provisional application No. 60/001,103, Jul. 13, 1995.

[30] Foreign Application Priority Data

Jul. 4, 1995 [GB] United Kingdom .................. 9513550
Jul. 4, 1996 [WO] WIPO ..................... PCT/GB96/01608

[51] Int. Cl.[7] .................................................. A61K 31/695
[52] U.S. Cl. ........................... 514/63; 556/406; 556/465; 552/296; 552/298; 552/299
[58] Field of Search ...................... 514/63, 682; 568/328; 556/406, 430, 432, 436, 437, 465; 560/8, 85, 107, 112, 113; 552/296, 298, 299

[56] References Cited

FOREIGN PATENT DOCUMENTS 0 300 218   6/1988   European Pat. Off. .

OTHER PUBLICATIONS

Aoyama et al, "New Methods and Reagents in Organic Synthesis . . . ," Heterocycles, vol. 30, No. 1, pp. 375–379, (1990).

Henton et al, "Chemistry of Quinone Derivatives. Quinone . . . ," J. Org. Chem., vol. 45, pp. 3422–3433 (1980).

Balzer et al, "Intramolecular Benzannulation Reactions of Manganese Carbene Complexes," J. Am. Chem. Soc., vol. 114, p. 8735–8736 (1992).

*Primary Examiner*—Sreeni Padmanabhan
*Attorney, Agent, or Firm*—Nixon & Vanderhye

[57] ABSTRACT

This invention relates to certain naphthoquinone derivatives of the general formula (1)

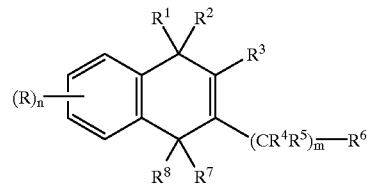

or a salt thereof, in which m, n, R, $R^1$, $R^2$, $R^3$, $R^4$, $R^5$, $R^6$, $R^7$, $R^8$ are as defined in the description; processes for their preparation; compositions containing such compounds and their use as a pesticide, such as a fungicide and, especially, an insecticide or an acaricide.

19 Claims, No Drawings

PESTICIDAL COMPOUNDS

This appln claims the benefit of U.S. Provisional application Ser. No. 60/001,103 filed Jul. 13, 1995.

This invention relates to certain naphthoquinone derivatives, a process for their preparation, compositions containing such compounds and their use as pesticides, such as fungicides and, especially, insecticides and/or acaricides.

DE3801743 A1 generically discloses compounds of the general formula

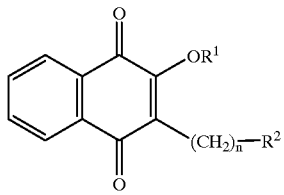

(A)

in which n is 0 to 12, $R^1$ represents hydrogen or an optionally substituted alkyl, aralkyl, alkylcarbonyl, (hetero)arylcarbonyl, alkoxycarbonyl, alkylsulphonyl or arylsulphonyl group, and $R^2$ represents a haloalkyl, optionally substituted (hetero)aryl or substituted cycloalkyl group, which are said to exhibit acaricidal and fungicidal activity. When $R^2$ represents a phenyl or cyclohexyl group, the list of preferred substituents includes tri-($C_{1-2}$ alkyl)silyl groups and, of these, a trimethylsilyl group is especially preferred. However, of the many compounds specifically disclosed which fall within formula I as defined above, only one compound is disclosed which contains such a substituent, that is the compound of Example 5 in which n is 0, $R^1$ is a hydrogen atom and $R^2$ is a 4-(trimethylsilyl)cyclohexyl group. Moreover, although data is provided which indicates that the compound of Example 5 exhibits some acaricidal and fungicidal activity, it is apparent that this compound is not the most pesticidally active compound of those compounds specifically disclosed in DE 3801743 A1.

It has now been discovered that certain naphthoquinone derivatives which bear a group attached to the naphthoquinone ring which includes at least one silicon atom as an integral part of the group rather than as part of an optional substituent exhibit superior pesticidal, for instance, fungicidal and/or, especially, insecticidal and/or acaricidal, activity and that many of these compounds are active against resistant strains of insects and/or acarids, especially resistant strains of aphids, mites and whitefly, as well as susceptible strains.

According to the invention there is therefore provided a compound of the general formula

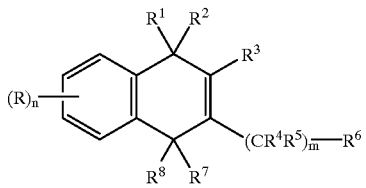

(I)

or a salt thereof, in which m is 0 or 1;

n represents an integer from 0 to 4:

each R independently represents a halogen atom or a nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl, aryl or aralkyl group;

$R^1$ and $R^2$ each independently represent an optionally substituted alkoxy group or together represent a group =O, =S or =N—$OR^9$, where $R^9$ represents a hydrogen atom or an optionally substituted alkyl group;

$R^3$ represents an optionally substituted alkyl group, a hydroxyl group, a group —OL where L is a leaving group or a group which in vivo is transformed into a group —$OL^1$ where $L^1$ is a leaving group;

$R^4$ and $R^5$, if present, each independently represent a hydrogen or halogen atom or an optionally substituted alkyl group or together with the interjacent carbon atom represent an optionally substituted cycloalkyl or cycloalkenyl group optionally containing at least one ring-silicon atom;

$R^6$ represents an optionally substituted group containing at least one silicon atom or, in the case where m is 1 and the —$CR^4R^5$-moiety contains at least one silicon atom, $R^6$ may additionally represent a hydrogen atom or an optionally substituted alkyl, alkenyl, alkynyl, cycloalkyl, cycloalkenyl, aryl, alkoxy, alkenyloxy, alkynyloxy, cycloalkoxy, cycloalkenyloxy or aryloxy group; and $R^7$ and $R^8$ independently represent an optionally substituted alkoxy group or together represent a group =O, =S or =N—$OR^9$, where $R^9$ is as previously defined.

When any of the foregoing groups $R^4$, $R^5$ and $R^6$ contain at least one silicon atom, the or each silicon atom forms an integral part of the group, that is, the or each silicon atom is a ring or chain atom, and is not a substituent on the group. Particularly the silicon atom is not a substituent on a carbocyclic ring but may be directly connected to such a ring only when it is part of a chain which includes the 1' position carbon atom of the carbocyclic ring.

When the compounds of formula I contain an alkyl, alkenyl or alkynyl substituent group, this may be linear or branched and may contain up to 12, preferably up to 6 and especially up to 4, carbon atoms. A cycloalkyl or cycloalkenyl group may contain from 3 to 8, preferably 4 to 7, carbon atoms. An aryl group may be any aromatic hydrocarbon group, especially a phenyl or naphthyl group. An aralkyl group may be any alkyl group as defined above which is substituted by an aryl group as defined above, especially a benzyl group.

When any of the foregoing substituents are designated as being optionally substituted, the substituent groups which are optionally present may be any one or more of those customarily employed in the development of pesticidal compounds and/or the modification of such compounds to influence their activity, persistence, penetration or other property. Specific examples of such substituents include, for example, halogen atoms, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl, phenyl and benzyl groups. Typically, 0–3 substituents may be present. When any of the foregoing substituents represents or contains an alkyl substituent group, this may be linear or branched and may contain up to 12, preferably up to 6, and especially up to 4, carbon atoms. When any of the foregoing substituents represents or contains an aryl or cycloalkyl moiety, the aryl or cycloalkyl moiety may itself be substituted by one or more halogen atoms, nitro, cyano, alkyl, haloalkyl, alkoxy or haloalkoxy groups. Preferably, the aryl moiety is a phenyl moiety and the cycloalkyl moiety contains from 3 to 8, especially 4 to 7, carbon atoms.

Compounds of formula I in which $R^3$ represents a hydroxyl group and the atom at the α- and β-positions, particularly the β-position, of the group $R^6$ is a silicon atom are synthetically less accessible than other compounds of formula I. It is therefore preferred that, if $R^3$ represents a hydroxyl group, then the atom at the α- and/or β-position of the group $R^6$ is not a silicon atom.

It is also preferred that R, if present, represents a halogen atom or a nitro, cyano, hydroxyl, $C_{1-4}$ alkyl, $C_{1-4}$haloalkyl, $C_{1-4}$alkoxy, $C_{1-4}$haloalkoxy, $C_{1-4}$alkylamino, di-$C_{1-4}$ alkylamino, $C_{1-4}$ alkoxycarbonyl, $C_{1-4}$alkylthio, $C_{1-4}$alkylsulphinyl or $C_{1-4}$alkylsulphonyl group.

More preferably, R, if present, represents a halogen atom or a $C_{1-4}$ alkyl, $C_{1-4}$ haloalkyl, $C_{1-4}$ alkoxy or $C_{1-4}$ haloalkoxy group.

Preferably, n is 0, 1 or 2 and it is especially preferred that n is 0.

It is also preferred that $R^1$ and $R^2$ each independently represent a $C_{1-4}$ alkoxy, especially a methoxy, group or together represent a group =O or =N—$OR^9$, where $R^9$ represents a hydrogen atom or a $C_{1-4}$ alkyl, especially a methyl, group.

It is especially preferred that $R^1$ and $R^2$ together represent a group =O.

When $R^3$ represents a group —OL where L is a leaving group or a group which in vivo is transformed into a group —$OL^1$ where $L^1$ is a leaving group, the leaving groups L and $L^1$ may be any group customarily employed as a leaving group. However, it is preferred that the leaving groups L and $L^1$ are such that the $pK_a$ value of the acids LOH and $L^1$OH in water is below 7, more preferably below 6 and especially below 5.

When $R^3$ represents a group which in vivo is transformed into a group —$OL^1$ where $L^1$ is a leaving group, it is preferred that the transformation occurs in a plant to be protected or in the pest, preferably by the action of enzymes within the plant or pest. For instance, if $R^3$ represents a β-acid group, such as —O—$CH_2CH_2CO$—OH where —$CH_2CH_2CO$—OH is not a leaving group, it may be subjected to enzymatic oxidation in vivo, by for example, a β-oxidase, to form a group —O—CO—$CH_2$—CO—OH where —CO—$CH_2$—CO—OH is a leaving group.

It is preferred that $R^3$ represents a group —$OR^{10}$ where $R^{10}$ represents a hydrogen atom, or a group —CO—$R^{11}$, —SO—$R^{11}$, —$SO_2$—$R^{11}$, —P(X)($OR^{12}$)($OR^{13}$), —P(X)($R^{12}$)($OR^{13}$), —P($OR^{12}$)($OR^{13}$) or —P($R^{12}$)($OR^{13}$) where $R^{11}$ represents a hydrogen atom, an optionally substituted alkyl, aryl or aralkyl group or a group —$NR^{12}R^{13}$; $R^{12}$ and $R^{13}$ independently represent a hydrogen atom or an optionally substituted alkyl group and X represents an oxygen or sulphur atom. When $R^{10}$ or $R^{11}$ represents an optionally substituted aryl or aralkyl group, it is preferred that the aryl group or moiety is a phenyl group or moiety and that the optional substituents are selected from halogen atoms, nitro and $C_{1-4}$ alkyl groups. Substitution at the 4-position of the phenyl ring is particularly preferred.

Preferably, $R^3$ represents a hydroxyl group or a group —O—CO—$R^{11}$ where $R^{11}$ represents a hydrogen atom or a $C_{1-12}$ alkyl, $C_{1-12}$ haloalkyl, $C_{1-12}$ hydroxyalkyl, $C_{1-12}$ carboxylalkyl, phenyl or benzyl group.

It is particularly preferred that $R^3$ represents a hydroxyl group or a group —O—CO—$R^{11}$ where $R^{11}$ represents a hydrogen atom or a $C_{1-6}$ alkyl, $C_{1-6}$ haloalkyl, phenyl or benzyl group.

In one preferred aspect, $R^4$ and $R^5$ may each independently represent a hydrogen atom or a $C_{1-4}$ alkyl, especially methyl, or $C_{1-4}$ haloalkyl, especially trifluoromethyl, group. More preferably, $R^4$ and $R^5$ both represent a hydrogen atom.

Alternatively, $R^4$ and $R^5$ together with the interjacent atom may represent a $C_{3-8}$ cycloalkyl group optionally substituted by one or more substituents selected from halogen atoms, $C_{1-4}$ alkyl and $C_{1-4}$ haloalkyl groups. More preferably, $R^4$ and $R^5$ together with the interjacent atom represent a $C_{3-8}$ cycloalkyl group optionally substituted by one or more halogen, especially chlorine or bromine, atoms. It is particularly preferred that $R^4$ and $R^5$ together with the interjacent atom represent an unsubstituted $C_{5-7}$ cycloalkyl group.

When $R^4$ and $R^5$ have any of the significations given in the immediately preceding two paragraphs, $R^6$ must represent a group containing at least one silicon atom. It is therefore preferred that $R^6$ represents an optionally substituted alkyl, alkenyl, alkynyl, cycloalkyl, cycloalkenyl, aryl, alkoxy, alkenyloxy, alkynyloxy, cycloalkoxy, cycloalkenyloxy or aryloxy group, each group containing at least one silicon atom and up to 20, especially up to 15, and preferably 2 to 12, carbon atoms.

More preferably, $R^6$ represents an alkyl, haloalkyl, alkoxyalkyl, alkoxy, haloalkoxy, alkoxyalkoxy, alkenyl, haloalkenyl or alkoxyalkenyl group, each group containing one or two silicon atoms and up to 20, especially up to 15, and preferably 2 to 12 carbon atoms.

It is further preferred that $R^6$ represents an alkyl or alkenyl group containing one silicon atom and up to 20, especially up to 15, and preferably 2 to 12 carbon atoms.

Preferred groups $R^6$ are of formula -$(A)_m$-Si$(R^{14})_3$ where m is as defined for formula (I) each $R^{14}$ is independently $C_{1-4}$ alkyl or with the interjacent silicon two such groups aform a siliacarbocyclic ring, and A is a $C_{1-20}$ alkyl or alkenyl group, which may be substituted with halogen, and which may be straight, branched or be or include a carbocyclic ring. Further preferred groups $R^6$ include silicon as a ring atom in an otherwise carbocyclic ring where it may be at any ring posistion, including the point of attachment to other groups such as an alkyl or alkenyl chain in $R^6$.

More preferably, $R^6$ represents a group —$(CH_2)_p$—Si$(R^{14})$ where p represents an integer from 1 to 15, preferably 1 to 10 and especially 1 to 6, and each $R^{14}$ independently represents a $C_{1-4}$ alkyl, especially methyl, group. Alternatively two groups $R^{14}$ may form a 3–8 membered silacarbocyclic, eg. silacycloalkyl, ring together with the interjacent silicon atom shown.

In another preferred aspect, $R^4$ and $R^5$ together with the interjacent carbon atom may represent a silacycloalkyl group containing from 3 to 8, preferably 5 to 7, ring atoms optionally substituted by one or more substituents selected from halogen atoms, $C_{1-4}$ alkyl and $C_{1-4}$ haloalkyl groups. More preferably, $R^4$and $R^5$ together with the interjacent carbon atom represent a silacycloalkyl group containing from 3 to 8, preferably 5 to 7, ring atoms optionally substituted by one or more halogen, especially chlorine or bromine, atoms. It is particularly preferred that $R^4$ and $R^5$ together with the interjacent carbon atom represent an unsubstituted silacycloalkyl group containing from 5 to 7 ring atoms. Preferably, the silacycloalkyl group contains one or two silicon atoms, more preferably only one silicon atom.

When $R^4$ and $R^5$ have any of the significations given in the immediately preceding paragraph, it is preferred that $R^6$ represents a hydrogen atom or an optionally substituted alkyl, alkenyl, alkynyl, cycloalkyl, cycloalkenyl, aryl, alkoxy, alkenyloxy, alkynyloxy, cycloalkoxy, cycloalkenyloxy or aryloxy group, each group optionally containing at least one silicon atom and up to 20, especially up to 15, and preferably 2 to 12 carbon atoms More preferably, $R^6$ represents a hydrogen atom or an alkyl, haloalkyl, alkoxyalkyl, alkoxy, haloalkoxy, alkoxyalkoxy, alkenyl, haloalkenyl or alkoxyalkenyl group, each group optionally containing one or two silicon atoms and up to 20, especially up to 15, and more preferably from 2 to 12 carbon atoms.

It is further preferred that $R^6$ represents an alkyl or alkenyl group optionally containing one silicon atom and up to 20, especially up to 15, and more preferably from 2 to 12 carbon atoms.

Preferably, $R^7$ and $R^8$ independently represent a $C_{1-4}$ alkoxy, especially a methoxy, group or together represent a group =O or =N—$OR^9$, where $R^9$ represents a hydrogen atom or a $C_{1-4}$ alkyl, especially a methyl, group.

It is especially preferred that $R^7$ and $R^8$ together represent a group =O.

A particularly preferred sub-group of compounds of formula I is that in which m is 1; n is 0; $R^1$ and $R^2$ both represent a methoxy group or together represent a group =O; $R^3$ represents a hydroxy, alkynoxy, (eg. ethanoyloxy) or aryloxyl (eg. benzoyloxy) group; $R^4$ and $R^5$ both represent a hydrogen atom; $R^6$ represents a trimethylsilyethyl, trimethylsilylethyl, trimethylsilylpropyl, trimethylsilylbutyl, trimethylsilylpentyl, trimethylsilylhexyl, trimethylsilylheptyl, trimethylsilyloctyl, trimethylsilylnonyl or trimethylsilyldecyl group; and $R^7$ and $R^8$ together represent a group =O.

The compounds of formula I may form salts when $R^3$ represents a hydroxyl group.

Suitable bases for forming such salts include inorganic bases, such as sodium hydroxide, potassium hydroxide and sodium carbonate, and organic bases, especially tertiary amines, such as triethylamine and pyrrolidine.

It should also be appreciated that some of the compounds of formula I are capable of existing as different geometric isomers and diastereomers. The invention thus includes both the individual isomers and mixtures of such isomers.

The present invention also provides a process for the preparation of a compound of formula I or a salt thereof as defined above which comprises reacting a compound of the general formula (II)

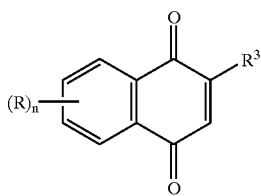

(II)

in which n, R and $R^3$ are as defined above with a carboxylic acid HOOC—$(CR^4R^5)_m$—$R^6$, where m, $R^4$, $R^5$ and $R^6$ are as defined above with the proviso that, when m is 0, the atom at the α-position of the group $R^6$ is not a silicon atom, in the presence of a free radical initiator, such as ammonium peroxysulphate and silver nitrate in a suitable solvent, such as aqueous acetonitrile, to form a compound of the general formula (III)

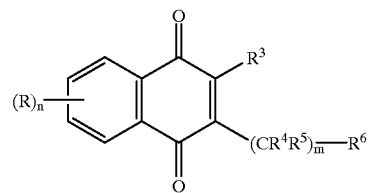

(III)

in which m, n, $R^3$, $R^4$, $R^5$ and $R^6$ are as defined above with the proviso that, when m is 0, the atom at the α-position of the group $R^6$ is not a silicon atom.

Compounds of formula III correspond to compounds of formula I in which $R^1$ and $R^2$ together and $R^7$ and $R^8$ together represent a group =O and may then be further reacted using various known derivatisation processes or combinations thereof to obtain further compounds of formula I, as desired.

For instance, compounds of formula II in which $R^3$ represents a group —O—CO—$C_6H_5$ are convenient starting materials and may be reacted as described above to form the corresponding compound of formula III. Compounds of formula I in which $R^3$ represents a hydroxyl group may then be prepared by reacting the compound of formula III in which $R^3$ represents a group —O—CO—$C_6H_5$ with a suitable base, for instance, an inorganic base, such as sodium hydroxide or potassium hydroxide, in the presence of a suitable solvent, such as tetrahydrofuran. Compounds of formula I in which $R^3$ represents a group —OL, where L is as defined above, may be prepared by reacting a compound of formula I in which $R^3$ represents a hydroxyl group with a compound Y-L, where Y represents a halogen atom, in the presence of an organic base, preferably a tertiary amine such as triethylamine, or an inorganic base, such as sodium carbonate. For instance, compounds of formula I in which $R^3$ represents a group —O—CO—$R^{11}$, where $R^{11}$ is as defined above, may be prepared by acylation of the hydroxyl group in a suitable compound of formula I, for instance, by using an acyl chloride $R^{11}$—CO—Cl in a suitable solvent, such as dichloromethane, in the presence of a base, such as triethylamine, or an acid anhydride in the presence of a base, such as pyridine. Alternatively, compounds of formula I in which $R^3$ represents a hydroxyl group may be reacted with a compound HO-L, where L is as defined above, in the presence of a dehydrating agent, such as dicyclohexylcarbodiimide. Compounds of formula I in which $R^3$ represents a group —OL, where L is as defined above, may also be prepared by reacting a metal salt of a compound of formula I in which $R^3$ represents a hydroxyl group, that is, $R^3$ represents a group —OM where M is a metal ion, with a compound Y-L as defined above.

Compounds of formula I in which $R^1$ and $R^2$ and/or $R^7$ and $R^8$ each independently represent an optionally substituted alkoxy group may be prepared by ketalisation of one or both carbonyl groups in a suitable compound of formula III, for instance, by using a suitable alcohol in basic or acidic conditions, such as potassium hydroxide in methanol.

Compounds of formula I in which $R^1$ and $R^2$ together and/or $R^7$ and $R^8$ together represent a thiocarbonyl group =S may be prepared by treating a suitable compound of formula III with a thiating agent, such as Lawesson's Reagent (2,4-bis(4-methoxyphenyl)-1,3-dithia-2,4-diphosphetane-2,4-disulphide), using protecting groups where required.

Compounds of formula I in which $R^1$ and $R^2$ together and/or $R^7$ and $R^8$ together represent an oxime group =N—$OR^9$, where $R^9$ is as defined above, may be prepared by treating a suitable compound of formula III with a hydroxylamine or alkoxylamine of formula R⁹O—NH₂, where R⁹ is as defined above, in the presence of a base, such as pyridine.

In an alternative process for preparing compounds of formula I, particularly in which m is 0 and the atom at the α-position of the group R⁶ is a silicon atom, a compound of the general formula (IV)

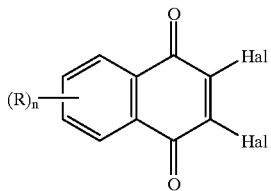

(IV)

where each Hal independently represents a halogen, preferably a chlorine or bromine, atom and n and R are as defined above, is reacted with a compound of the general formula Z-R⁶, where Z represents a halogen, preferably a chlorine or bromine, atom and R⁶ is as defined above particularly with the proviso that the atom at the α-position of the group R⁶ is a silicon atom, in the presence of an organometallic reagent, such as butyl lithium, in a solvent, such as diethyl ether or tetrahydrofuran, at low temperature, preferably −70° C. to −120° C., to form a compound of the general formula (V)

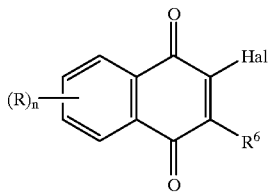

(V)

in which n, R, R⁶ and Hal are as defined above, particularly with the proviso that the atom at the α-position of the group R⁶ is a silicon atom.

The compound of formula V may then be reacted with a suitable base, for instance, an inorganic base, such as sodium hydroxide or potassium hydroxide, to form the corresponding compound of formula I in which R³ represents a hydroxyl group.

Combinations of the derivatisation processes described above may then be performed to obtain further compounds of formula I, as desired.

Compounds of formula II and IV are known compounds or can be prepared from known compounds by processes analogous to known processes.

As mentioned above, the compounds of general formula I have been found to have pesticidal, for instance, fungicidal and/or, especially, insecticidal and/or acaricidal, activity. Accordingly, the invention further provides a pesticidal composition which comprises a carrier and, as active ingredient, a compound of formula I or a salt thereof as defined above. A method of making such a composition is also provided which comprises bringing a compound of formula I as defined above into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

The compositions of the invention may contain from 0.001 to 95% by weight of the active ingredient of formula I. Preferably the compositions contain from 0.001 to 25% by weight of the active ingredient when they are in ready-to-use form. However, higher concentrations, for instance, up to 95%, may be present in compositions to be sold as concentrates for dilution before use.

The compounds of the invention may be mixed with a variety of appropriate inert carriers such as solvents, diluents and/or surface-active agents to form dusts, granular solids, wettable powders, mosquito coils or other solid preparations or emulsions, emulsifiable concentrates, sprays, aerosols or other liquid preparations. Suitable solvents and diluents include water, aliphatic and aromatic hydrocarbons such as xylene or other petroleum fractions and alcohols such as ethanol. Surface-active agents may be of an anionic, cationic or non-ionic type. Anti-oxidants or other stabilisers may also be included as well as perfumes and colourings. These inert carriers may be of the type and in proportions such as are conventionally used in pesticidal compositions.

In addition to these inert carriers, the compositions of the invention may also contain one or more further active ingredients. These further active ingredients may be other compounds which exhibit pesticidal activity and these other compounds may exhibit a synergistic effect with the compounds of the present invention.

The compounds of formula I as defined above may be used to control pest infestation in domestic, horticultural, agricultural, medical or veterinary environments. Thus, according to another aspect of the present invention there is provided the use as a pesticide, for instance, a fungicide and/or, especially, an insecticide and/or acaricide, of a compound of formula I or a salt thereof as defined above or a composition as defined above.

The present invention also provides a method of combating pests, such as fungi and/or, especially, insects and/or acarids, at a locus which comprises treating the locus with a compound of formula I or a salt thereof as defined above or a composition as defined above. Preferably, the locus comprises the pests per se or environments subject to or subjected to attack by pests. More preferably, the locus comprises the pests per se, stored food material, plants or animals subject to or subjected to attack by pests, seeds of such plants or the medium in which such plants are growing or are to be grown. Specifically, compounds of formula I and compositions as defined above may be used in a domestic environment for spraying rooms to combat infestation by houseflies or other insects, in a horticultural or agricultural environment for treatment of stored crops, especially cereals, or to spray growing crops such as cotton or rice to combat infestation by fungi, insects or other pests, and in a medical or veterinary environment, for instance, as a cattle spray to prevent or treat infestation by insects or other pests.

The present invention will now be further described by way of illustration only by reference to the following non-limiting examples. In these, structures of compounds are confirmed by assigned ¹³C nmr shifts (in ppm.), listed in the order: bicyclic system; CH₂'s (and =CH's if present); Si(alk)₃ group; other groups. Further examples falling within the scope of the claims will occur to those skilled in the art in the light of these.

EXAMPLES

Example 1

Preparation of 2-Benzoyloxy-3-(2'-trimethylsilylethyl-1,4-naphthoquinone
(Formula I: m=1; n=0; R¹ and R² together and R⁷ and R⁸ together both represent =O: R³=—O—CO—C₆H₅: R⁴=R⁵=H; R⁶=—CH₂Si(CH₃)₃)

2-Benzoyloxy-1,4-naphthoquinone (1.39 g, 5 mmol), trimethylsilylpropionic acid (1.09 g, 7.5 mmol) and silver nitrate (523 mg, 3 mmol) were suspended in 40 ml aqueous acetonitrile (1:1) and then heated to 65° C. Ammonium persulphate (1.71 g, 7.5 mmol) in 20 ml water was added slowly and dropwise over 30 minutes to the mixture. The reaction mixture was stirred at this temperature for a further hour and then cooled, diluted with diethyl ether and the aqueous phase removed. The organic extract was washed with saturated sodium bicarbonate solution, then brine and dried over anhydrous magnesium sulphate. After concentration in vacuo, the crude material was chromatographed using petroleum ether/ethyl acetate as eluent to give 2-benzoyloxy-3-(2'-trimethylsilylethyl)-1,4-naphthoquinone (879 mg) which was recrystallised from methanol, m.pt.: 92–95° C. NMR peaks at: 184.4, 178.2, 150.3, 142.6, 134.0, 133.8, 132.1, 130.9, 126.6, 126.6; 18.8, 16.2; −2.0; 163.8, 128.0, 128.7, 130.4, 134.2 (PhCO).

Example 2

Preparation of 2-Hydroxy-3-(2'-trimethylsilylethyl)-1,4-naphthoquinone (Formula I: m=1; n=0; $R^1$ and $R^2$ together and $R^7$ and $R^8$ together both represent =O; $R^3$=—OH; $R^4$=$R^5$=H; $R^6$=—$CH_2Si(CH_3)_3$)

2-Benzoyloxy-3-(2'-trimethylsilylethyl)-1,4-naphthoquinone (270 mg, 0.71 mmol) obtained as in Example 1 above in tetrahydrofuran (10 ml) was treated with 2N sodium hydroxide (0.73 ml, 1.42 mmol) and the mixture stirred overnight at room temperature. The reaction mixture was concentrated in vacuo and the residue taken up in diethyl ether and acidified to pH 2 with 1N hydrochloric acid. The organic phase was washed with brine, dried over anhydrous magnesium sulphate and concentrated in vacuo. The crude material was chromatographed using ethyl acetate/petroleum ether as eluent to give 2-hydroxy-3-(2'-trimethylsilylethyl)-1,4-naphthoquinone (163 mg) which was recrystallised from hexane, m. pt. 98–100° C. NMR peaks at: 184.6, 181.6, 152.2, 134.7, 132.9, 129.4, 127.3, 126.6, 126.0; 17.6, 15.7; −1.9.

Example 3

Preparation of 2-Hydroxy-3(5'-trimethylsilylpentyl)-1,4-naphthoquinone (Formula I: m=1; n=0; $R^1$ and $R^2$ together and $R^7$ and $R^8$ together both represent =O; $R^3$=—OH; $R^4$=$R^5$=H; $R^6$=—$(CH_2)_4Si(CH_3)_3$)

2-Hydroxy-3(6'-trimethylsilylhexyl)-1,4-naphthoquinone (337 mg, 1.02 mmol), prepared from 2-benzoyloxy-1,4-naphthoquinone and trimethylsilylheptanoic acid by the method of Example 1 followed by the method of Example 2, was dissolved in dioxane (2.5 ml) under nitrogen. Sodium carbonate (120 mg) in water (2.5 ml) was added followed by an excess of 30% (w/v) hydrogen peroxide (200 μl). The mixture was heated at 70° C. for 40 minutes during which time the reaction mixture turned from red to colourless. The reaction mixture was allowed to cool and 20% (w/v) copper sulphate solution (100 μl) was added and the solution stirred until bubbling ceased. 25% (w/v) sodium hydroxide solution (2 ml) and 20% (w/v) copper sulphate solution (5 ml) were then added and the reaction mixture heated at 70° C. for 30 minutes. The mixture was allowed to cool and acidified to pH 2 with 1N hydrochloric acid. The product was extracted into diethyl ether and the ether extract was then washed with brine, dried over anhydrous magnesium sulphate and concentrated in vacuo. The crude material was chromatographed using 5% diethyl ether/hexane as eluent to give 2-hydroxy-3(5'-trimethylsilylpentyl)-1,4-naphthoquinone (202 mg) which was recrystallised from hexane, m. pt. 73–75° C. NMR peaks at: 184.6, 181.4, 153.0, 134.8, 132.9, 132.7, 129.4, 126.7, 126.0, 124.8; 33.6, 27.9, 33.7, 23.2, 16.5; −1.7.

Example 4

Preparation of 2-ethanoyloxy-3-(2'-trimethylsilylethyl)-1,4-naphthoquinone (Formula I: m=1; n=0; $R^1$ and $R^2$ together and $R^7$ and $R^8$ together both represent =O; $R^3$=—O—CO—$CH_3$; $R^4$=$R^5$=H; $R^6$=—$CH_2Si(CH_3)_3$)

2-Benzoyloxy-3-(2'-trimethylsilylethyl)-1,4-naphthoquinone (346 mg, 0.92 mmol) obtained as in Example 1 above was hydrolysed as in Example 2 above and the hydrolysed material was acetylated directly by the addition of pyridine (6 ml) and acetic anhydride (3 ml). After standing overnight, the volatiles were removed in vacuo. The crude material was chromatographed using ethyl acetate/petroleum ether as eluent to give 2-ethanoyloxy-3-(2'-trimethylsilylethyl)-1,4-naphthoquinone (265 mg) which was recrystallised from hexane m. pt. 85–87° C. NMR peaks at: 184.3, 178.2, 149.8, 142.2, 134.0, 133.7, 132.0, 130.8, 126.5, 126.4; 18.6, 16.1; −2.1; 167.9, 20.2 ($COCH_3$).

Example 5

Preparation of 2-Hydroxy-3-(2'-trimethylsilylethyl)-1,4-naphthoquinone, 1-dimethyl Acetal Formula I: m=1; n=0; $R^1$=$R^2$=—$OCH_3$; $R^3$=—OH; $R^4$=$R^5$=H; $R^6$=—$CH_2Si(CH_3)_3$); $R^7$ and $R^8$ together represent =O 2-Ethanoyloxy-3-(2'-trimethylsilylethyl)-1,4-naphthoquinone (3 g) obtained as in Example 4 was dissolved in methanol (100 ml), water (5 ml) and potassium carbonate (1.5 g). The reaction mixture was stirred at room temperature for 2 hours and then diluted with water (about 400 ml). The mixture was then extracted with diethyl ether, dried over anhydrous sodium sulphate and the solvent evaporated to give 2-hydroxy-3-(2'-trimethylsilylethyl)-1,4-naphthoquinone, 1-dimethyl acetal as a pale yellow solid, m. pt. 102–104° C. NMR peaks at: 183.6, 158.4, 135.2, 133.4, 132.7, 130.0, 126.2, 125.6, 125.2, 97.3; 16.8, 16.3; −2.1; 51.9 (2×OMe).

Examples 6 to 13

By processes similar to those described in Examples 1 to 5 above, further compounds of formula I were prepared as detailed in Table 1 below. In this table, the compounds are identified by reference to formula I.

TABLE 1

(In the following examples m = 1; n = 0; $R^1$ & $R^2$ together and $R^7$ & $R^8$ together both represent a group = O; $R^4$ = $R^5$ = H)

| Example No. | R3 | R6 | m.pt. (° C.) | $n_D$ |
|---|---|---|---|---|
| 6 | —OH | —$Si(CH_3)_3$ | 76–78 | |
| 7 | —OH | —$(CH_2)_2$—$Si(CH_3)_3$ | 70–71 | |
| 8 | —OH | —$(CH_2)_3$—$Si(CH_3)_3$ | 74–76 | |

TABLE 1-continued (In the following examples m = 1; n = 0; $R^1$ & $R^2$ together and $R^7$ & $R^8$ together both represent a group = O; $R^4 = R^5 = H$)

| Example No. | R3 | R6 | m.pt. (° C.) | $n_D$ |
|---|---|---|---|---|
| 9 | —OH | —$(CH_2)_5$—$Si(CH_3)_3$ | 43–45 | |
| 10 | —OH | —$(CH_2)_6$—$Si(CH_3)_3$ | 38–42 | |
| 11 | —OH | —$(CH_2)_7$—$Si(CH_3)_3$ | 37–40 | |
| 12 | —OH | —$(CH_2)_8$—$Si(CH_3)_3$ | 36 | |
| 13 | —OH | —$(CH_2)_9$—$Si(CH_3)_3$ | | 1.5356 |

NB.$n_D$ signifies refractive index for the sodium D lines.

NMR peaks were observed as follows;

Example 6: NMR peaks at: 184.7, 180.8, 151.3, 134.4, 132.9, 132.9, 129.7, 126.7, 126.0, 125.5; 15.0; −0.8.

Example 7: 184.7, 181.5, 154.0, 134.8, 132.9, 132.8, 129.5, 127.6, 126.0, 125.6; 27.1, 22.9, 17.0; −1.7.

Example 8: 184.6, 181.4, 152.9, 134.7, 132.9, 132.8, 129.4, 126.7, 126.0, 124.8; 32.1, 24.2, 23.1, 16.4; −1.7.

Example 9: 184.6, 181.4, 153.0, 134.7, 132.8, 132.6, 129.4, 126.7, 126.0, 124.8; 33.4, 29.5, 28.2, 23.8, 23.3, 16.5; −1.7.

Example 10: 184.7, 181.5, 153.0, 134.8, 132.9, 132.8, 129.4, 126.8, 126.0, 124.9; 33.5, 29.7, 29.2, 28.3, 23.9, 23.4, 16.6; −1.6.

Example 11: 184.7, 181.5, 153.0, 134.8, 132.9, 132.8, 129.4, 126.7, 126.0, 124.9; 33.6, 29.8, 29.4, 29.3, 28.3, 23.9, 23.3, 16.6; −1.6.

Example 12: 184.7, 181.5, 153.0, 134.8, 132.9, 132.8, 129.5, 126.8, 126.0, 124.9; 33.6, 29.8, 29.5, 29.4, 29.3, 28.3, 23.9, 23.4, 16.7; −1.7.

Example 13: 184.6, 181.4, 153.0, 134.7, 132.9, 132.8, 129.4, 126.7, 126.0, 124.8; 33.6, 29.8, 29.6, 29.6, 29.4, 29.3, 28.3, 23.9, 23.3, 16.6; −1.7.

Example 14

Preparation of 2-Hydroxy-3(8-(dimethylethylsilyl) octyl)-1,4-naphthoquinone

Formula I: m=1, n=0; $R^1$ & $R^2$ together and $R^7$ & $R^8$ together both represent a group =O; $R^3$=—OH; $R^4$=$R^5$=H and $R^6$=—$(CH_2)_7Si(CH_3)_2CH_2CH_3$.

To magnesium turnings (1.98 g, 81.5 mmol) at room temperature was added dropwise a solution of 1,8-dibromooctane (11.1 g, 40.8 mmol) in dry THF (50 ml). When the effervescence had ceased the mixture was refluxed for 2 h to prepare octyl dimagnesium dibromide. After cooling to room temperature, a solution of chlorodimethylethylsilane (5.00 g, 40.8 mmol) in THF (5 ml) was slowly added. After addition the reaction was refluxed for a further 1 h. Gaseous carbon dioxide was passed through the cooled reaction mixture for 30 minutes before diluting with ether (50 ml) and acidifying with dilute hydrochloric acid. The aqueous layer was separated and extracted further with ether (3×25 ml). The combined ether layers were washed with water (2×25 ml), saturated sodium chloride solution (50 ml) and dried (MgSO$_4$). Filtration and evaporation of the solvents under reduced pressure yielded a white waxy solid which was extracted with hexane (3×50 ml). The combined hexane extracted were evaporated under reduced pressure to yield a colourless liquid (5.94 g). This liquid was reacted with 2-benzoyloxy-1,4-naphthoquinone, by the method described in Example 1 followed by the method described in Example 2 to give 2-hydroxy-3(8-(dimethylethylsilyl) octyl)-1,4-naphthoquinone (753 mg), which was recrystallised from hexane, m. pt.39–41° C. NMR peaks at: 184.7, 181.5, 152.9, 134.8, 132.9, 132.8, 129.4, 126.8, 126.0, 124.8; 33.7, 29.8, 29.4, 29.3, 28.3, 23.9, 23.4, 14.8; 7.4, 6.9, −3.9.

Examples 15–17

By a process identical to that described for Example 13, further compounds of formula I were prepared as detailed in Table 2 below. In this table, the compounds are identified by reference to formula I.

TABLE 2

(In all the following examples m = 1, n = 0, $R^1$ & $R^2$ together and $R^7$ & $R^8$ together both represent a group = O, $R^4 = R^5 = H$)

| Example No. | $R^3$ | $R^6$ | m.pt.(° C.) |
|---|---|---|---|
| 15 | —OH | —$(CH_2)_7$—$SiEt_3$ | 51–53 |
| 16 | —OH | —$(CH_2)_7$—$SiPr_3$ | 48–50 |
| 17 | —OH | —$(CH_2)_7$—$SiMe_2Pr$ | 45–47 |

NMR peaks were observed as follows;

Example 15

NMR peaks at: 184.7, 181.5, 153.0, 134.8, 132.9, 132.9, 129.4, 126.8, 126.1, 124.8; 33.9, 29.8, 29.4, 29.3, 28.3, 23.8, 23.4, 11.3; 7.5, 3.3.

Example 16

NMR peaks at: 184.7, 181.5, 153.0, 134.8, 132.9, 132.8, 129.5, 126.8, 126.0, 124.9; 34.0, 29.9, 29.5, 29.3, 28.3, 23.9, 23.4, 12.6; 18.7, 17.5, 15.6.

Example 17

NMR peaks at: 184.7, 181.5, 153.1, 134.8, 133.0, 132.8, 129.5, 126.8, 126.0, 124.9; 33.7, 29.9, 29.4, 29.3, 28.3, 23.9, 23.4, 18.0; 18.4, 17.4, 15.3, −3.3.

Example 18

Preparation of 2-Hydroxy-3-(8-(1-methyl-(tetramethylenesilyl))octyl)-1,4-naphthoquinone Formula I: m=1, n=0; $R^1$ & $R^2$ together and $R^7$ & $R^8$ together both represent a group =O; $R^3$=—OH; $R^4$=$R^5$=H and $R^6$=—$(CH_2)_7SiCH_3(CH_2)_4$.

A solution of dibromobutane (20.0 g, 92.6 mmol) in dry THF (100 ml) was slowly added to magnesium turnings (4.5 g, 185 mmol). After addition was complete the mixture was refluxed for 1 h and cooled to room temperature. A solution of trimethylsilylchloride (13.8 g, 92.6 mmol) in THF (10 ml) was added dropwise and refluxing was continued for 30 minutes. The cooled solution was added dropwise to a preformed solution of octyl dimagnesium dibromide, as described in Example 14. The mixture was refluxed for 1 h before cooling to room temperature and gaseous carbon dioxide was bubbled through the solution for 30 minutes. The residue was acidified with dilute hydrochloric acid and extracted with ether (4×50 ml). The combined ether layers were washed with water (2×50 ml), saturated sodium chloride solution (50 ml) and dried (MgSO$_4$). Filtration and evaporation of the solvent under reduced pressure gave an off-white waxy solid, that was extracted with hexane (3×50 ml). The combined hexane extracts were evaporated under reduced pressure to yield a pale yellow oil. This liquid was reacted with 2-benzoyloxy-1,4-naphthoquinone, by the method described in Example 1 followed by the method described in Example 2 to give 2-hydroxy-3(8-(1-methyl-(tetramethylenesilyl))octyl)-1,4-naphthoquinone (161 mg), m.pt 42–44° C. NMR peaks at: 184.7, 181.5, 153.0, 134.8, 132.9, 132.8, 129.4, 126.8, 126.1, 124.8; 33.5, 29.8, 29.4, 29.3, 28.3, 24.3, 23.4; 27.4, 15.1, 11.8, −3.2.

Example 19

Preparation of 2-Hydroxy-3-(8-(1-methyl-(pentamethylenesilyl))octyl)-1,4-naphthoquinone Formula I: m=1, n=0; $R^1$ & $R^2$ together and $R^7$ & $R^8$ together both represent a group =O; $R^3$=—OH; $R^4$=$R^5$=H and $R^6$=—$(CH_2)_7SiCH_3(CH_2)_5$.

By a process identical to that described in Example 17, but replacing dibromobutane with dibromopentane, gave 2-hydroxy-3-(8-(1-methyl-(pentamethylenesilyl))octyl)-1,4-naphthoquinone (10 mg), m.pt. 38–40° C. NMR peaks at: 184.7, 181.5, 153.0, 134.8, 133.0, 132.9, 129.5, 126.8, 126.1, 124.9; 33.6, 29.8, 29.4, 29.3, 28.3, 23.7, 23.4, 14.1; 30.2, 24.5, 12.9, −4.8.

Example 20

Preparation of 2-Hydroxy-3-(3-trimethylsilyl-1-propenyl)-1,4-naphthoquinone

Formula I: m=0, n=0; $R^1$ & $R^2$ together and $R^7$ & $R^8$ together both represent a group =O; $R^3$=—OH; $R^4$=$R^5$=H and $R^6$=—CH=CH—CH$_2$Si(CH$_3$)$_3$.

To a stirred solution of 3-trimethylsilylpropanol (5.00 g, 37.8 mmol) in dichloromethane (120 ml) at room temperature was added pyridinium chlorochromate (16.3 g, 75.6 mmol). The mixture was stirred for 2 h and then filtered through silica gel, eluting with ether. The filtrate was evaporated under reduced pressure to give a colourless liquid (3.96 g). To a stirred solution of the previously prepared liquid (1.00 g) in dichloromethane (30 ml) at room temperature, was added 2-hydroxy-1,4-naphthoquinone (1.11 g, 6.40 mmol), and pyrrolidine (569 mg, 8.00 mmol). The reaction was stirred for 15 h before p-toluenesulphonic acid (3.04 g, 16.0 mmol) was added, and stirring at room temperature was continued for a further 24 h and refluxing for 3 h. The mixture was cooled and the solvent evaporated under reduced pressure. The residue was dissolved in ether (50 ml) and washed with water (2×25 ml), dilute hydrochloric acid (25 ml), water (25 ml), saturated sodium chloride solution (25 ml), and dried (MgSO$_4$). Filtration and evaporation of the solvent under reduced pressure and chromatography eluting with hexane/ether gave 2-hydroxy-3-(3-trimethylsilyl-1-propenyl)-1,4-naphthoquinone (123 mg) m. pt 72–74° C. NMR peaks at: 184.6, ca 182, 150.5, 134.7, 133.0, 132.8, ca 129, 126.9, 125.8, ca 120; 142.5, 117.0, 27.4; −1.8.

Example 21

Preparation of 2-Ethanoyloxy-3-(9-trimethylsilylnonyl)-1,4-naphthoquinone (Formula I: m=1; n=0; $R^1$ and $R^2$ together and $R^7$ and $R^8$ together both represent =O: $R^3$=—O—CO—CH$_3$: $R^4$=$R^5$=H: $R^6$=—(CH$_3$)$_8$Si(CH$_3$)$_3$ By a process identical to that described in Example 4 on 2-hydroxy-3-(9-trimethylsilylnonyl)-1,4-naphthoquinone, Example 12, gave 2-ethanoyloxy-3-(9-trimethylsilylnonyl)-1,4-naphthoquinone, m. pt.45–47° C. NMR peaks at: 184.5, 178.1, 151.1, 139.9, 134.0, 133.8, 132.1, 130.9, 126.7, 126.6; 33.6, 29.7, 29.4, 29.4, 29.3, 28.5, 24.3, 24.0, 16.7; −1.6; 168.0, 20.4 (COCH$_3$).

Example 22

Preparation of 2-Propanoyloxy-3-(9-trimethylsilylnonyl)-1,4-naphthoquinone (Formula I: m=1; n=0; $R^1$ and $R^2$ together and $R^7$ and $R^8$ together both represent =O; $R^3$=—O—COCH$_2$CH$_2$CH$_3$; $R^4$=$R^5$=H; $R^6$=—(CH$_2$)$_8$Si(CH$_3$)$_3$ To a stirred solution of 2-hydroxy-3-(9-trimethylsilylnonyl)-1,4-naphthoquinone, Example 12, (100 mg, 0.27 mmol) in dry dichloromethane (10 ml) at room temperature was added pyridine (0.5 ml) and, after 3 minutes, propanoyl chloride (62 mg, 0.67 mmol). The reaction was stirred for 2 h before diluting with dichloromethane (50 ml), washing with water (2×30 ml), dilute hydrocholic acid (30 ml), saturated sodium chloride solution (30 ml) and dried (MgSO$_4$). Filtration and evaporation of the solvent under reduced pressure and chromatography, eluent hexane/ether, gave 2-propanoyloxy-3-(9-trimethylsilylnonyl)-1,4-naphthoquinone (112 mg). m. pt. 41–43° C. NMR peaks at: 184.6, 178.2, 151.2, 139.8, 134.0, 133.7, 132.1, 130.9, 126.7, 126.5, 33.6, 29.7, 29.4, 29.4, 29.3, 29.3, 28.5, 24.3, 23.9, 16.7, −1.6; 171.6, 27.3, 9.1 (COCH$_2$CH$_3$).

Example 23

Preparation of 2-Vinylcarbonato-3-(9-trimethylsilylnonyl)-1,4-naphthoquinone (Formula I: m=1; n=0; $R^1$ and $R^2$ together and $R^7$ and $R^8$ together both represent =O; $R^3$=—O—CO—O—CH=CH$_2$; $R^4$=$R^5$=H; $R^6$=—(CH$_2$)$_8$Si(CH$_3$)$_3$ To a stirred solution of 2-hydroxy-3-(9-trimethylsilylnonyl)-1,4-naphthoquinone, Example 12, (100 mg, 0.27 mmol) in dry dichloromethane (10 ml) at room temperature was added pyridine (0.5 ml) and, after 3 minutes, vinyl chloroformate (43 mg, 0.40 mmol). The reaction was stirred for 2 h before diluting with dichloromethane (50 ml), washing with water (2×30 ml), dilute hydrocholic acid (30 ml), saturated sodium chloride solution (30 ml) and dried (MgSO$_4$). Filtration and evaporation of the solvent under reduced pressure and chromatography, eluent hexane/ether, gave 2-vinylcarbonato-3-(9-trimethylsilylnonyl)-1,4-naphthoquinone (79 mg), $n_D$ 1.5123 NMR peaks at: 184.6, 178.0, 149.9, 139.9, 134.6, 134.3, 132.3, 130.9, 127.1, 126.8, 33.9, 30.6, 30.0, 29.7, 29.6, 29.6, 29.5, 28.8, 24.5, 24.2, 16.9, −1.3; 149.8, 142.8, 99.8 (—O—CO—O—CH=CH$_2$).

Example 24

Preparation of 2-Ethoxymethoxy-3-(9-trimethylsilylnonyl)-1,4-naphthoquinone (Formula I: m=1: n=0; $R^1$ and $R^2$ together and $R^7$ and $R^8$ together both represent =O; $R^3$=—O—CH$_2$OCH$_2$CH$_3$; $R^4$=$R^5$=H; $R^6$=—(CH$_2$)$_8$Si(CH$_3$)$_3$ To a stirred solution of 2-hydroxy-3-(9-trimethylsilylnonyl)-1,4-naphthoquinone, Example 12, (500 mg, 2.06 mmol) in dry dichloromethane (20 ml) at room temperature was added diisopropylethylamine (1.33 g, 10.3 mmol) and, after 3 minutes, ethoxymethyl chloride (831 mg, 10.3 mmol) in dichloromethane (5 ml). The reaction was stirred for 1 h before diluting with dichloromethane (30 ml), washing with water (2×20 ml), dilute hydrochloric acid (20 ml), saturated sodium chloride solution (20 ml) and drying (MgSO$_4$). Filtration and evaporation of the solvent under reduced pressure and chromatography, eluent hexane/ether, gave 2-ethoxymethoxy-3-(9-trimethylsilylnonyl)-1,4-naphthoquinone (567 mg), $n_D$ 1.5182. NMR peaks at: 185.3, 181.6, 155.5, 137.1, 133.8, 133.2, 132.0, 131.4, 126.3, 126.2, 33.6, 30.1, 29.5, 29.4, 29.3, 28.9, 24.1, 23.9, 16.7, −1.6; 96.9, 65.8, 15.0 (O—CH$_2$—O—CH$_2$CH$_3$).

Example 25

Preparation of 2-Hydroxy-3-((1',4',4'-trimethyl-4-silacyclohexylmethyl)-1,4-naphthoquinone (Formula I as Example 24 with $R^3$=OH: $R^6$=—(C$_5$H$_8$Si)(CH$_3$)$_3$)

To a stirred solution of 4,4-dimethyl-4-silacyclohexanone (prepared as described in Sonderquist and Negron; J. Org. Chem.) (900 mg, 6.32 mmol), ethylcyanoacetate (716 mg, 6.32 mmol) and piperidine (215 mg) in benzene (30 ml) at room temperature was added acetic acid (760 mg) and the mixture was refluxed under azeotropic conditions for 2½ hours. The reaction mixture was cooled to room temperature, diluted with ether (30 ml) and washed with water (2×25 ml), saturated sodium chloride solution (25 ml) and dried (MgSO$_4$). Filtration and evaporation of solvents under reduced pressure and chromatography using hexane/ether eluent gave a colourless liquid (0.52 g).

This liquid was dissolved in ether (5 ml) and added dropwise to a solution of methyl magnesium bromide (30 mg, 1.8 mmol) in ether (20 ml) stirring at 0° C., under nitrogen. The mixture was stirred for a further 2 hours before diluting with ether (25 ml), water (10 ml), and acidifying with dilute hydrochloric acid. The aqueous layer was separated and extracted further with ether (2×25 ml) and the combined ether extracts were washed with water (2×20 ml). saturated with sodium chloride solution (20 ml) and dried (MgSO$_4$). filtration and evaporation of solvents under reduced pressure gave a colourless oil which was treated with potassium hydroxide (550 mg) in ethylene glycol and refluxed for 16 hours. The reaction mixture was cooled to room temperature, diluted with water (40 ml) and washed with ether (2×25 ml). The aqueous layer was acidified with dilute hydrochloric acid and extracted with ethyl acetate (4×25 ml). The combined extracts were washed with water (2×20 ml), saturated sodium chloride solution (20 ml) and dried (MgSO$_4$). Filtration and evaporation of solvents under reduced pressure gave a near colourless liquid (300 mg).

This liquid was subjected to a process similar to that described in Examples 1 and 2 above to give 2-hydroxy-3-((1',4',4'-trimethyl-4-silacyclohexyl)methyl)-1,4-naphthoquinone.

Example 26
Pesticidal Activity

Pesticidal activity was assessed against houseflies, mustard beetles, mites and whitefly using the following methods.

Houseflies (MD) (*Musca domestica*)

Female flies were treated on the thorax with a one microliter drop of test compound dissolved in acetone. Two replicates of 15 flies were used at each dose rate and 6 dose rates were used per compound under test. After treatment, the flies were maintained at a temperature of 20°±1° C. and kill was assessed 24 and 48 hours after treatment. LD$_{50}$ values were calculated in micrograms of test compound per fly (see Sawicki et al., Bulletin of the World Health Organisation, 35, 893 (1966) and Sawicki et al., Entomologia and Exp. Appli 10, 253, (1967).

Mustard beetles (PC) (*Phaedon cochleariae* Fab)

A one microliter drop of an acetone solution of the test compound was applied ventrally to adult mustard beetles using a micro drop applicator. The treated insects were maintained for 48 hours after which time kill was assessed. Two replicates each of 20 to 25 mustard beetles were used at each dose level and 5 dose levels were treated comparably. LD$_{50}$ values were calculated as for houseflies.

Mites (TU) (*Tetranychus urticae*)

25 adult female mites were immersed in 35 µl of a solution of the test compound in a 1:4 acetone-water mixture for 30 seconds. The treated insects were maintained at 21°±2° C. and kill was assessed 72 hours after treatment. Mites exhibiting repetitive (non-reflex) movement of more than one locomotory appendage after this period were recorded as alive. Three replicates of 25 mites each were used at each dose rate and 5 or 6 dose rates were used per compound under test. LC$_{50}$ values were calculated in ppm of the solution of the test compound per insect. The test was carried out using a susceptible strain of mites (GSS) supplied by Schering, AG, Berlin.

Whitefly (BT) (*Bemisia tabaci*)

Acetone solutions (0.100 ml) of the test compounds were placed in 10 ml glass vials and evaporated with rotation to deposit a film of the compound. Thirty adult whiteflies were placed inside the vial, then after 60 minutes, the treated insects were transferred onto untreated cotton leaf discs which were kept moist on a bed of agar gel. The temperature was maintained at 25° C. and mortality assessed after 48 hours. Three replicates were used at each of 5 to 7 dose levels per compound. LC$_{50}$ values were calculated by using a computer software package ("Polo-PC" available from LeOra Software, Berkeley, Calif.). (See M. R. Cahill and B. Hackett in Proceedings Brighton Crop Protection Conference, 1992). The test was carried out using a susceptible strain of whitefly (SUD-S) which was collected in Sudan in 1978 from cotton.

The results of these tests are set out in Table 3 below. The values given are LD$_{50}$ (µg/insect) or LC$_{50}$ (ppm solution of test compound) unless otherwise specified.

TABLE 3

| Compound Example No | MD (LD50) | PC (LD50) | TU (GSS) (LC50) | BT (SUD-S) (LC50) |
|---|---|---|---|---|
| 1 | >20 | >20 | 110 | — |
| 2 | 0.69 | 0.45 | 38 | 2.6 |
| 3 | 1.3 | c.1.0 | 2.8 | 6.8 |
| 4 | c.20 | c.2.0 | 45 | 2.9 |
| 5 | >20 | c.20 | 41 | — |
| 6 | — | c.20 | — | 1.7 |
| 7 | 4.4 | c.8 | 6.4 | c.9 |
| 8 | 1.8 | c.1 | 9.2 | c10 |
| 9 | 1.8 | c.1 | 4.5 | 100% |
| 10 | 1.7 | c.0.2 | 0.31 | 8.2 |
| 11 | 2.3 | c.1 | 0.51 | 14.6 |
| 12 | 2.8 | 0.13 | 0.9 | 8.6 |
| 13 | 9.9 | c.0.6 | 2.2 | — |
| 14 | — | c2 | c2 | 15 |
| 15 | — | c2 | 5.2 | 22 |
| 16 | — | >20 | — | 79%* |
| 17 | — | c.1 | 8.4 | 13 |
| 18 | — | c.2 | 3.6 | — |
| 19 | — | c.2 | — | 13%* |
| 20 | — | >20 | 21 | 30 |
| 21 | c2 | c2 | 2.0 | <100 |
| 22 | — | c2 | c20 | c100 |
| 23 | — | c2 | c50 | 32%* |
| 24 | — | c20 | — | 19%* |

* = kill at 100 ppm.
— = not done.

Example 27
Aphicidal activity

Activity against resistant (R) and susceptible (S) strains of aphid (*Myzus persicae*) and *Aphis gossypiae* was assessed using the following two methods.

Topical application

Batches of 10–15 apterous adults were removed from stock cultures and placed on leaf discs (35 mm in diameter) cut from chinese cabbage and held on an agar bed (25 mm deep) in disposable plastic containers (30 mm high). Using a Burkhard micro-applicator aphids were dosed individually with a 0.25 µm droplet of chemical diluted to the required concentration in acetone. control insects were dosed with acetone only. Mortality and other effects were scored at 24 hour intervals up to and including 72 hour post-treatment, the end-point to which the results relate.

Aphid-dip

Entrapment rings of fluon were painted halfway up the inside of 4 cm lengths of glass tubing (1.5 cm diameter), and squares of insect-proof gauze were attached to one end of each tube by elastic bands. Fifteen apterous adults were then gently transferred into the tubes using a sable-hair brush, and the tube sealed with a second gauze square.

Tubes containing aphids were dipped into insecticide solutions for 10 seconds, dried on blotting paper, and then inverted and tapped to cause treated aphids to fall to the unimmersed end of each tube. Handling mortality (usually zero or very slight) was scored after 1 hour, when aphids were transferred onto chinese cabbage leaf-discs (35 mm diameter) on an agar bed (25 mm in depth) in disposable plastic containers (30 mm high) and confined by applying a ring of fluon to the exposed lip of the container. Containers were stored upright, without lids, in a constant environment facility maintained at 25° C. under continuous room lighting. Mortality was assessed at 24, 48 and 72 hours. Two replicates of 15 aphids each were used at each dose rate and 5 or 6 dose rates were used per compound under test.

The test was carried out using a susceptible strain of aphids (US1L) collected in the field in East Anglia, UK and an extremely resistant strain of aphids (794Jz) ($R^3$ esterase, sensitive ACHE) collected from glasshouses in the UK.

The results of this test are set out in Table 5 below. The values given are % mortality corrected for control data. The control comprised the test solution without active ingredient.

TABLE 4

TOPICAL APHID RESULTS
All results quoted as % kill at 100 ppm unless otherwise indicated.

| EXAMPLE NO. | M.P. USIL | M.P. 794JZ |
|---|---|---|
| 2 | 45 | |
| 3 | 100 | |
| 7 | 45 | |
| 8 | 90 | 100$^{(1)}$ |
| 9 | 100 | |
| 10 | 100 | |
| 11 | 100 | 95 |
| 12 | 89 | |
| 13 | 90 | |
| 14 | 74 | |
| 15 | 58 | |
| 16 | 24 | |
| 17 | 88 | |
| 18 | 59 | |
| 21 | 66$^{(2)}$ | 89 |
| 22 | 37 | |
| 23 | 63 | |
| 24 | 16 | |

$^{(1)}$1000 ppm
$^{(2)}$125 ppm

TABLE 5

APHID-DIP RESULT
All quoted as % kill at 100 ppm

| EXAMPLE NO. | M.P. USIL | M.P. 794JZ | A.G. 81–171B |
|---|---|---|---|
| 2 | 77 | 54 | 63 |
| 3 | 100 | | 100 |
| 4 | 19 | 19 | |
| 7 | 90 | | 57 |

TABLE 5-continued

APHID-DIP RESULT
All quoted as % kill at 100 ppm

| EXAMPLE NO. | M.P. USIL | M.P. 794JZ | A.G. 81–171B |
|---|---|---|---|
| 8 | 90 | 100 | |
| 9 | 100 | | 71 |
| 10 | 100 | | 100 |
| 11 | 100 | | 100 |
| 12 | 100 | 61 | 93 |
| 13 | 90 | | 83 |
| 21 | 66 | | |

MP = Myzus
AP = Aphis

Example 28

Fungicidal Activity

Fungitoxicity of coded compounds to isolates of *Aspergillus niger*, *Pyricularia oryzae* (=*Magnaporthe grisea*) and *Rhizoctonia solani* was tested in vitro.

Each compound was incorporated into potato dextrose agar in solvent (50/50 ethanol/acetone) at 0.5 ml solvent per 250 ml agar while the autoclaved agar was still molten and cooled to 50° C. Each compound was tested at a single concentration (100 mg $l^{-1}$).

Each test, usually of two compounds, included three control treatments: a standard fungicide (carbendazim at 1 or 5 mg $l^{-1}$ or prochloraz at 1 mg $l^{-1}$); ethanol/acetone only; no additions. The fungicides used as standards may be considered as representative of active, commercially available compounds.

Each fungus was tested on agar in four Petri dishes per treatment, with three replicate fungal colonies per plate (one colony for *R. solani*). *A. niger* and *R. solani* were incubated for 4 days at 20–25° C., and *P. oryzae* for 7 days. Increase in colony diameter was then measured and used to determine activity.

The results of these tests are set out in Table 6 below. The values given are % inhibition of growth in colony diameter in agar plates.

TABLE 6

| Compound of Example No. | Fungus | Activity at 100 mg $l^{-1}$ | Activity at 5 mg $l^{-1}$ | Activity at 1 mg $l^{-1}$ |
|---|---|---|---|---|
| 2 | A. niger | 18 | | |
| 2 | P. oryzae | 67 | | |
| 2 | R. solani | 35 | | |
| Prochloraz | A. niger | | | 97.8 |
| Carbendazim | P. oryzae | | 99.8 | 14.7 |
| Carbendazim | R. solani | | 82.4 | 3.3 |

In addition, tests have shown that the compounds of formula I exhibit good fungicidal activity against a broad spectrum of fungi which cause diseases in both cereal and broad leaved crops. Particularly, good activity has been observed against fungi of the genera Erysiphe, especially *Erysiphe graminis,* and Botrytis, especially *Botrytis fabae* and *Botrytis cinerea,* as well as the genera Rhizoctonia, Pyricularia and Aspergillus as illustrated above.

Table 7 below shows the pesticidal activity of comparative naphthoquinone compounds of the prior art in order to better illustrate the relative efficacy of the compounds of the invention. The activities listed were obtained using the methods outlined in Examples 27 and 28 above.

Regarding the prior art naphthoquinone of DE 3801743; EP 0300218 A1 lists its activity against Tetranychus as less than the corresponding tertiary butyl compound (see Tabelle A of EP 0300218 A1). That t-butyl compoud has been tested by the present inventors and found to have $LC_{50}$ values of 44 ppm/insect against Tetranycus and 18 ppm against Bemisia; $LD_{50}$ values of 16 µg/insect against Musca and 0.53 µg/insect against Phaedon and give 19% kill against Myzus in the tests set out above.

TABLE 7

Comparative Examples $R^1R^2$ and $R^7R^8$ == 0; $R^3$ = OH

| Naphthalene 3 position | PC $LD_{50}$ (µg/insect) | MD $LD_{50}$ (µg/insect) | MP % kill 100 ppm | TU $LC_{50}$ (ppm/ insect) | BT $LC_{50}$ (ppm/ insect) |
|---|---|---|---|---|---|
| —H | NA | NA | — | NA | NA |
| —CH$_3$ | NA | NA | — | NA | NA |
| —CH$_2$CH$_3$ | NA | NA | — | NA | NA |
| —(CH$_2$)$_2$CH$_3$ | c10 | NA | — | c1000 | 80 |
| —(CH$_2$)$_3$CH$_3$ | c5 | c10 | — | 65 | 13 |
| —(CH$_2$)$_4$CH$_3$ | c7 | NA | — | 16 | 17 |
| —(CH$_2$)$_5$CH$_3$ | c7 | c20 | 0 | 170 | 9.4 |
| —(CH$_2$)$_7$CH$_3$ | 0.78 | 1.9 | — | c1000 | 19 |
| —(CH$_2$)$_9$CH$_3$ | 1.9 | NA | — | 5.5 | >100 |
| —(CH$_2$)$_{10}$CH$_3$ | c0.4 | NA | — | 1.4 | >100 |
| —(CH$_2$)$_{11}$CH$_3$ | NA | NA | 0 | <60 | >100 |
| —(CH$_2$)$_{13}$CH$_3$ | NA | NA | — | 1.3 | NA |

In order to exemplify the preparation of naphthoquinone rings bearing substituents at the 5, 6, 7 and/or 8 positions the following Examples 29 to 31 falling outside the scope of the present invention are provided.

Example 29

Preparation of 2-(t-Butyl)-3-hydroxy-6-methyl-naphthalene-1,4-dione and 2-(t-Butyl)-3-hydroxy-7-methyl-naphthalene-1,4-dione (a) Preparation of 6-methyl-naphthalene-1,4-dione A solution of 1,4-benzoquinone (13.9 g, 128 mmol) and isoprene (13.1 ml, 131 mmol) was stirred in glacial acetic acid (44 ml) for 68 hours at room temperature. The mixture was diluted with water (44 ml) and refluxed for 1½ hours. The mixture was cooled to room temperature and acetic acid (84 ml) and chromic acid [chromium trioxide (29.4 g) in water (30 ml)] was added sequentially, before refluxing for a further 1½ hours. After cooling, the mixture was diluted with water (200 ml) and extracted with ether (3×50 ml). The combined ether fractions were washed with dilute sodium hydroxide solution (2M; 2 15×50 ml), water (2×50 ml), saturated sodium chloride solution (50 ml) and dried over magnesium sulphate. Filtration and evaporation of solvent under reduced pressure, and repeated recrystallisation from petroleum ether yielded the title compound (7 g).

(b) 2-Amino-6 and 7-methyl-1,4-naphthalene-1,4-diones

To a stirred solution of 6-methyl naphthalene-1,4-dione (2.1 g, 12 mmol) in glacial acetic acid (60 ml) at room temperature was added a solution of sodium azide (1.58 g) in water (5 ml). The mixture was stirred for 2 days before diluting with water (200 ml) and, after stirring for a further 15 minutes, was filtered. The filtrate was neutralised with sodium bicarbonate and extracted with chloroform (3×25 ml). The combined chloroform extracts were washed with saturated sodium bicarbonate solution, brine and dried (CaSO$_4$) Filtration and evaporation of solvent under reduced pressure and silica gel chromatography yielded the title compound (100 mg) as a 3:2 mixture of isomers.

(c) 2-Hydroxy-6- and -7-methyl-naphthalene-1,4-diones

The aminomethyl naphthalene-1,4-dione mixture from (b) (200 mg) was refluxed in water (20 ml) and concentrated sulphuric acid (10 ml) for 20 minutes. The cooled mixture was poured into ice/water (50 g) and extracted with ether (3×25 ml). The combined ether extracts were washed with water, saturated NaHCO$_3$, water, saturated NaCl solution and dried (MgSO$_4$). Filtration and evaporation of solvent and purification by silica gel column chromatography yielded the title compound (68 mg).

(d) Preparation of 2-(t-butyl)-3-hydroxy-6 and 7-methyl-3-hydroxy-naphthalene-1,4-diones Standard peroxysulphate/silver nitrate radical addition on the aminomethyl compound (64 mg, 0.34 mmol), trimethylacetic acid (52 mg, 0.51 mmol), yielded the title compound as a 3:2 mixture of isomers (12 mg).

Example 30

Preparation of 2-(t-Butyl)-6 and 7-Dimethyl-3-hydroxy-naphthalene-1,4-diones

Steps (a) to (d) above were repeated, replacing isoprene with 2,3-dimethyl-1,3-butadiene.

Example 31

Preparation of 2-(t-Butyl)-3-hydroxy-5 and 8-Methyl-1,4-naphthalene-1,4-diones

Steps (a) to (d) above were repeated, replacing isoprene with piperylene.

(a) Preparation of 6-methyl-1,4-naphthalene-1,4-dione

A solution of 1,4-benzoquinone (13.9 g, 128 mmol) and isoprene (13.1 ml, 131 mmol) was stirred in glacial acetic acid (44 ml) for 68 hours at room temperature. The mixture was diluted with water (44 ml) and refluxed for 1½ hours. The mixture was cooled to room temperature and acetic acid (84 ml) and chromic acid [chromium trioxide (29.4 g) in water (30 ml)] was added sequentially, before refluxing for a further 1½ hours. After cooling, the mixture was diluted with water (200 ml) and extracted with ether (3×50 ml). The combined ether fractions were washed with dilute sodium hydroxide solution (2M; 2×50 ml), water (2×50 ml), saturated sodium chloride solution (50 ml) and dried over magnesium sulphate. Filtration and evaporation of solvent under reduced pressure, and repeated recrystallisation from petroleum ether yielded the title compound (7 g).

What is claimed is:

1. A compound of the general formula

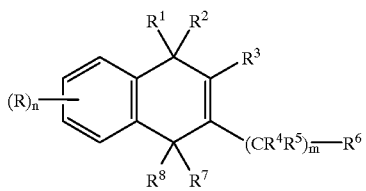

(1)

or a salt thereof, in which m is 0 or 1;

n represents an integer from 0 to 4;

each R independently represents a halogen atom or a nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl, aryl or aralkyl group;

$R^1$ and $R^2$ each independently represent an optionally substituted alkoxy group or together represent a group =O, =S or =N—$OR^9$, where $R^9$ represents a hydrogen atom or an optionally substituted alkyl group;

$R^3$ represents a hydroxyl group, or a group —OL where L is a leaving group or a group which in vivo is transformed into a group -$L^1$ where $L^1$ is a leaving group;

$R^4$ and $R^5$, if present, each independently represent a hydrogen or halogen atom or an optionally substituted alkyl group or together with the interjacent carbon atom represent an optionally substituted cycloalkyl or cycloalkenyl group optionally containing at least one ring-silicon atom;

$R^6$ represents an optionally substituted group containing at least one silicon atom or, in the case where m is 1 and the —$CR^4R^5$-moiety contains at least one silicon atom, $R^6$ may additionally represent a hydrogen atom or an optionally substituted alkyl, alkenyl, alkynyl, cycloalkyl, cycloalkenyl, aryl, alkoxy, alkenyloxy, alkynyloxy, cycloalkoxy, cycloalkenyloxy or aryloxy group; and $R^7$ and $R^8$ independently represent an optionally substituted alkoxy group or together represent a group =O, =S or =N—$OR^9$, where $R^9$ is as previously defined;

wherein, when $R^6$ represents an optionally substituted group containing at least one silicon atom, at least one of the silicon atoms of $R^6$ is not directly attached to a carbocylic ring.

2. A compound according to claim 1 in which R, if present, represents a halogen atom or a nitro, cyano, hydroxyl, $C_{1-4}$ alkyl, $C_{1-4}$ haloalkyl, $C_{1-4}$ alkoxy, $C_{1-4}$ haloalkoxy, $C_{1-4}$ alkylamino, di-$C_{1-4}$ alkylamino, $C_{1-4}$ alkoxycarbonyl, $C_{1-4}$ alkylthio, $C_{1-4}$ alkylsulphinyl or $C_{1-4}$ alkylsulphonyl group.

3. A compound according to claim 1 in which n is 0.

4. A compound according to claim 1 in which $R^1$ and $R^2$ each independently represent a $C_{1-4}$ alkoxy group or together represent a group =O or =N—$OR^9$, where $R^9$ represents a hydrogen atom or a $C_{1-4}$ alkyl group.

5. A compound according to claim 1 in which $R^3$ represents a group —$OR^{10}$ where $R^{10}$ represents a hydrogen atom, an optionally substituted alkyl, aryl or aralkyl group or a group —CO—$R^{11}$, —SO—$R^{11}$, —$SO_2$—$R^{11}$, —P(X)($OR^{12}$)($OR^{13}$), —P(X)($R^{12}$)($OR^{13}$), —P($OR^{12}$)($OR^{13}$) or —P($R^{12}$)($OR^{13}$) where $R^{11}$ represents a hydrogen atom, an optionally substituted alkyl, aryl or aralkyl group or a group —$NR^{12}R^{13}$, $R^{12}$ and $R^{13}$ independently represent a hydrogen atom or an optionally substituted alkyl group and X represents an oxygen or sulphur atom.

6. A compound according to claim 1 in which $R^3$ represents a hydroxyl group or a group —O—CO—$R^{11}$ where $R^{11}$ represents a hydrogen atom or a $C_{1-12}$ alkyl, $C_{1-12}$ haloalkyl, $C_{1-12}$ hydroxyalkyl, $C_{1-12}$ carboxylalkyl, phenyl or benzyl group.

7. A compound according to claim 1 in which $R^4$ and $R^5$ each independently represent a hydrogen atom or a $C_{1-4}$ alkyl group.

8. A compound according to claim 1 in which $R^4$ and $R^5$ together with the interjacent atom represent a $C_{3-8}$ cycloalkyl group optionally substituted by one or more substituents selected from halogen atoms, $C_{1-4}$ alkyl and $C_{1-4}$ haloalkyl groups.

9. A compound according to claim 1 in which $R^6$ represents an alkyl, haloalkyl, alkoxyalkyl, alkoxy, haloalkoxy, alkoxyalkoxy, alkenyl, haloalkenyl or alkoxyalkenyl group, each group containing one or two silicon atoms and up to 20 carbon atoms.

10. A compound according to claim 1 in which $R^4$ and $R^5$ together with the interjacent carbon atom represent a silacycloalkyl group containing from 3 to 8 ring atoms optionally substituted by one or more substituents selected from halogen atoms, $C_{1-4}$ alkyl or $C_{1-4}$ haloalkyl groups.

11. A compound according to claim 10 in which $R^6$ represents a hydrogen atom or an alkyl, haloalkyl, alkoxyalkyl, alkoxy, haloalkoxy, alkoxyalkoxy, alkenyl, haloalkenyl or alkoxyalkenyl group, each group optionally containing one or two silicon atoms and up to 12 carbon atoms.

12. A compound according to claim 1 in which $R^7$ and $R^8$ independently represent a $C_{1-4}$ alkoxy group or together represent a group =O or =N—$OR^9$, where $R^9$ represents a hydrogen atom or a $C_{1-4}$ alkyl group.

13. A compound as claimed in claim 1 wherein $R^6$ is of the formula -(A)$_m$-Si($R^{14}$) where m is as defined for formula (I), each $R^{14}$ is independently $C_{1-4}$ alkyl or two of these groups together with the interjacent silicon atom form a $C_{3-8}$ silacarbocyclic ring, and A is a $C_{1-20}$ alkyl or alkenyl group, which may be substituted with halogen, and which may be straight, branched or be or include a carbocyclic ring.

14. A compound as claimed in claim 1 wherein $R^6$ includes silicon as a ring atom in an otherwise carbocyclic ring.

15. A compound as claimed in claim 1 wherein $R^6$ represents a group —($CH_2$)$_p$—Si($R^{14}$)$_3$ where p represents an integer from 1 to 15, and each $R^{14}$ independently represents a $C_{1-4}$ alkyl group or two groups $R^{14}$ form a 3–8 membered silacarbocyclic ring together with the interjacent silicon atom shown.

16. A pesticidal composition which comprises a carrier and, as active ingredient, a compound of formula I or a salt thereof according to claim 1.

17. A method of combating pests at a locus which comprises treating the locus with a compound of formula I or a salt thereof according to claim 1 or a composition according to claim 16.

18. A compound as claimed in claim 15 wherein p represents an integer from 1 to 10.

19. A compound as claimed in claim 15, wherein p represents an integer from 1 to 6.

* * * * *